US005672494A

United States Patent [19]
Palsson et al.

[11] Patent Number: 5,672,494
[45] Date of Patent: *Sep. 30, 1997

[54] METHODS OF INCREASING RATES OF INFECTION BY DIRECTING MOTION OF VECTORS

[75] Inventors: Bernhard Ø. Palsson; Michael F. Clarke; Alice S. Y. Chuck, all of Ann Arbor, Mich.

[73] Assignee: The University of Michigan, Ann Arbor, Mich.

[*] Notice: The term of this patent shall not extend beyond the expiration date of Pat. No. 5,534,423.

[21] Appl. No.: 472,479

[22] Filed: Jun. 7, 1995

Related U.S. Application Data

[63] Continuation of Ser. No. 134,105, Oct. 8, 1993, Pat. No. 5,534,423.

[51] Int. Cl.$^6$ .................................................. C12N 15/64
[52] U.S. Cl. ............................................................ 435/172.3
[58] Field of Search ............................... 435/172.1, 172.3, 435/173.9; 935/52, 55, 56, 57

[56] References Cited

U.S. PATENT DOCUMENTS

| | | | |
|---|---|---|---|
| 1,316,789 | 9/1919 | Grimwood | 210/474 |
| 3,839,155 | 10/1974 | McAleer et al. | 435/298.2 |
| 4,159,933 | 7/1979 | Allington et al. | 204/543 |
| 4,164,464 | 8/1979 | Allington et al. | 204/600 |
| 4,201,845 | 5/1980 | Feder et al. | 435/297.2 |
| 4,301,010 | 11/1981 | Eddleman et al. | 210/406 |
| 4,339,537 | 7/1982 | Sogi et al. | 435/240.243 |
| 4,632,761 | 12/1986 | Bowers et al. | 210/650 |
| 5,036,006 | 7/1991 | Sanford et al. | 435/172.3 |
| 5,139,951 | 8/1992 | Butz et al. | 435/297.5 |
| 5,260,211 | 11/1993 | Matsuda et al. | 435/240.24 |
| 5,399,493 | 3/1995 | Emerson et al. | 435/172.3 |

FOREIGN PATENT DOCUMENTS

| | | |
|---|---|---|
| 252333 | 6/1987 | European Pat. Off. . |
| 9211355 | 9/1992 | WIPO . |
| WO93/05815 | 4/1993 | WIPO . |
| WO93/08270 | 4/1993 | WIPO . |
| WO93/17090 | 9/1993 | WIPO . |
| WO94/09145 | 4/1994 | WIPO . |
| WO95/12392 | 5/1995 | WIPO . |
| 9519427 | 7/1995 | WIPO . |

OTHER PUBLICATIONS

Russel, Stephen J. "Retroviral Vectors Displaying Functional Antibody Fragments." *Nucleic Acids Res.* 21:1081–1085 (1993).
Lynch and Miller, "Production of High–titer Helper Virus–free Retroviral Vectors by Cocultivation of Packaging Cells with Different Host Ranges." *J. Virology.* 65:3887–3890 (1991).
Cassel et al., "Retroviral–mediated Gene Transfer into CD34–Enriched Human Peripheral Blood Stem Cells." *Experimental Hematology.* 21:585–591 (1993).
Bodine et al., "Development of a High–titer Retrovirus Producer Cell Line Capable of Gene Transfer into Rhesus Monkey Hematopoietic Stem Cells." *Proc. Natl. Acad. Sci. USA.* 87:3738–3742 (1990).
Hidalgo et al., "Characterization of the Unstirred Water Layer in Caco–2 Cell Monolayers Using a Novel Diffusion Apparatus." *Pharma. Res.* 8:222–227 (1991).
Grass and Sweetana, "In Vitro Measurement of Gastrointestinal Tissue Permeability Using a New Diffusion Apparatus." *Pharma. Res.* 5:372–376 (1988).
Costar Transwell Application and Selection Guide—Selected unnumbered pages (Sep., 1991).
Verma, Inder, M. "Gene Therapy." *Sci. Amer.* 84:68–84 (Nov. 1990).
Bluestone, Mimi "Genes in a Bottle." *Bio/Tech.* 10:132–136 (1992).
Kaufman, Randal J. *Gene Expression Technology* "Vectors Used for Expression in Mammalian Cells." *Meth. Enzy.* 185:487–511 (1990).
Kriegler, Michael *Gene Expression Technology.* "Assembly of Enhancers, Promoters, and Splice Signals to Control Expression of Transferred Genes." *Meth. Enzy.* 185:512–527 (1990).
Keown, Wayne A. et al., *Gene Expression Technology.* "Methods for Introducing DNA into Mammalian Cells." *Meth. Enzy.* 185:527–537 (1990).
Cussler, E. L. *Diffusion Mass Transfer in Fluid Systems.* Cambridge University Press. New York, New York. pp.75–78 (1984).
Kriegler, Michael *Gene Transfer and Expression, A Laboratory Manual.* W. H. Freeman and Company. New York. New York. pp.23–61, 161–164 (1990).
Dunny, Gary M. et al., "Improved Electroporation and Cloning Vector System for Gram–Positive Bacteria." *App. Envirn. Micro.* 57:1194–1201 (1991).
Gaertig, Jacek and Gorovsky, Martin A. "Efficient Mass Transformation of *Tetrahymena Thermophila* by Electroporation of Conjugants." *Proc. Natl. Acad. Sci. USA* 89:9196–9200 (1992).
New Brunswick Scientific Co., Inc. Catalog (1966).
Bunnell, Bruce A. et al., "High–efficiency Retroviral–Mediated Gene Transfer into Human and Nonhuman Primate Peripheral Blood Lymphocytes". *Proc. Natl. Acad. Sci. USA* 92:7739–7743 (1995).
Kompier et al, Enzyme Microb. Technol., Oct., 1991, vol. 13: pp. 822–827.

*Primary Examiner*—Mindy Fleisher
*Assistant Examiner*—Terry A. McKelvey
*Attorney, Agent, or Firm*—Campbell & Flores LLP

[57] ABSTRACT

This invention provides methods of increasing the frequency of contact between vectors and stationary target cells in an apparatus containing them which involves causing the vectors to move towards the target cells with motion above and beyond random Brownian motion. The methods of this invention include causing the vectors to move in the direction of the cells by (1) causing flow-through of a liquid containing the vectors through or past a cell bed, (2) moving charged vectors towards the target cells by electrodiffusion and (3) centrifuging vectors and cells to cause settling of vectors onto the cells.

4 Claims, 9 Drawing Sheets

METHODS OF INCREASING RATES OF INFECTION BY DIRECTING MOTION OF VECTORS

This application is a continuation of application Ser. No. 08/134,105, filed Oct. 8, 1993 now U.S. Pat. No. 5,534,423.

BACKGROUND OF THE INVENTION

This invention relates generally to genetic engineering, and more specifically, to methods of increasing infection efficiency.

Scientists now routinely introduce genetic material into prokaryotic or eukaryotic cells to obtain the expression of heterologous genes. The application of this technology to human cells forms the basis for the burgeoning field of gene therapy. Typical methods include incorporating DNA directly into cells, for example, by calcium phosphate precipitation, and using vector-mediated infection. Scientists have used a wide variety of viruses as gene-transfer vectors. In particular, non-competent retroviruses have proved useful because they allow the stable introduction of genetic material into the chromosome of the infected target cell.

The process of retroviral infection involves many steps. In the initial step the virus comes in contact with the cell. Next, the viral RNA is internalized. Reverse transcription follows. Then the viral DNA enters the nucleus. Finally the virally derived DNA is integrated into the target cell's chromosomes. This step is believed to require cell division.

Retroviruses are assembled by so-called packaging cell lines. Scientists have developed two methods to infect a target cell with a retrovirus. First, one may co-culture the target cell with the packaging cell line. This approach has proven successful, but unfortunately it represents the clinically less attractive procedure. There is the risk of contaminating the infected target cells with cells from the packaging line, with subsequent risks.

Second, one may culture a bed of target cells and add to them spent medium from the packaging cell line. Scientists believe that this approach is limited by the concentration of the virus in the spent medium. It has proven difficult to obtain high titer supernatants from packaging cell lines because the viruses tends to disintegrate rapidly. In any case, attempts to increase the concentration of the virus has not led yet to a dramatic increase in rates of infection.

Thus, there exists a need for methods to increase the rate of infection of target cells by retroviral vectors. The present invention satisfies this need and provides related advantages as well by providing methods to direct to motion of vectors towards the target cells.

SUMMARY OF THE INVENTION

This invention provides a method of increasing the frequency of contact between vectors and stationary target cells in an apparatus containing them by causing the vectors to move towards the target cells over and above the movement caused by random Brownian motion.

This invention also provides the method of moving the vectors towards the target cells in which the vectors are contained in a liquid which is moved towards the target cells. In one embodiment of this invention, the apparatus includes a container having a porous surface which supports the target cells, wherein the container contains the liquid in contact with the porous surface, and the liquid is caused to move through the porous surface.

In another embodiment of this method, the apparatus further includes a centrifuge for spinning the container, and the method involves allowing the liquid to move through the porous membrane under the force of enhanced gravity created by spinning the container in the centrifuge.

In another embodiment of this method, the apparatus includes target cells plated on the face of a spinable disk and the method involves causing the vectors to move towards the cells by spinning the disk around an axis of rotation essentially perpendicular to the face of the disk, and directing a stream of the liquid towards the cells and substantially along the axis of rotation.

This invention also provides the method of causing the vectors to move towards the target cells by applying electrostatic force to the vectors. In one embodiment, the apparatus comprises an electrophoresis unit having first and second chambers separated by an ion-permeable membrane, the first chamber having an electrolytic fluid and a negative electrode in contact therewith, the second chamber having an electrolytic liquid and a positive electrode in contact therewith; and means for applying voltage across the positive and negative electrodes. The apparatus contains negatively charged vectors and target cells plated on the surface of the ion-permeable membrane in the first chamber.

This invention also provides the method of causing the vectors to move towards the cells by applying elevated gravitational force to induce sedimentation of the virus onto the target cells. In one embodiment, the apparatus includes a centrifuge having a rotor which has a surface which supports the target cells under centrifugal force and a liquid containing the vectors in contact with the surface.

DETAILED DESCRIPTION OF THE INVENTION

Figure 1:
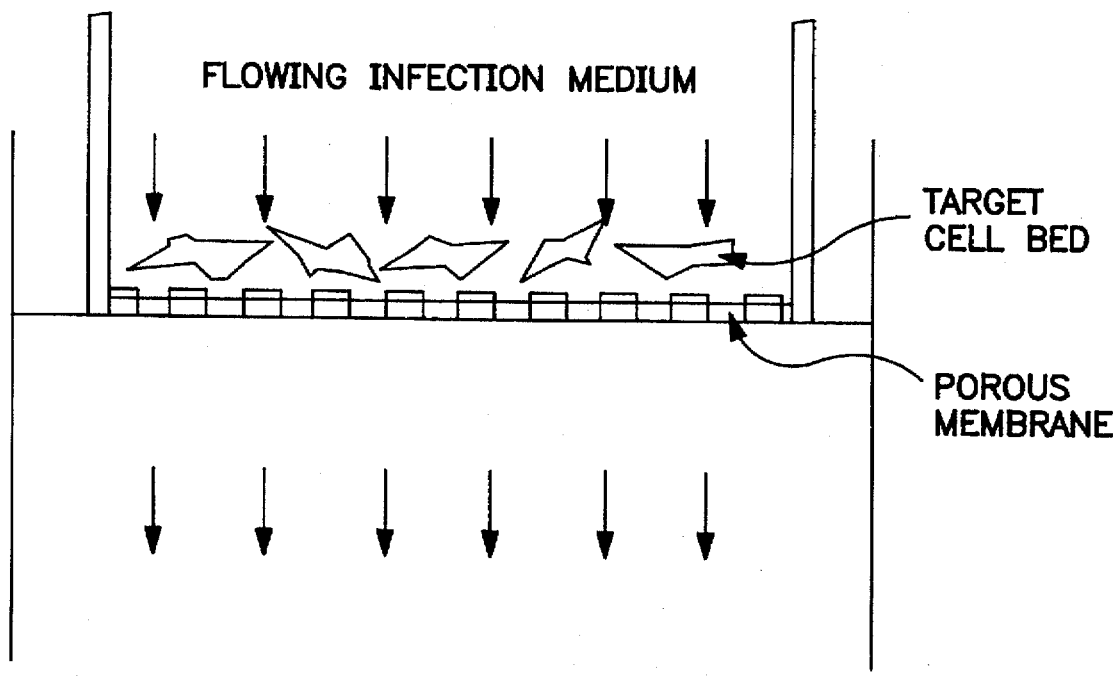
FIG. 1 depicts an embodiment of this invention in which a liquid infection medium containing the vectors are moved past the target cell bed and through a porous membrane by convective flow.

This invention provides methods that dramatically improve the infection efficiency of target cells by a vector by significantly increasing the number of contacts between vectors and target cells in a infection system. These methods are particularly useful for increasing infection rates by vectors having short half-lives, such as retroviruses. In a infection system comprising murine amphotropic virus and CV-1 cells, results demonstrate infection rates 10 to 30 times greater than that obtained using currently available methods.

This invention results from the application of a physico-chemical approach to the problem of cell infection. Infection requires physical contact between a vector and a target cell. Contact, in turn, is limited by two processes: the diffusion of the vector and the degradation of the vector. Each process has a characteristic time constant from which one can determine its rate.

The average time for a vector to travel a particular distance in one dimension is given by the classical Einstein equation for Brownian motion. (See, for example, E. L. Cussler, *Diffusion, Mass Transfer in Fluid Systems*, (1984)):

$$t_{diff} = l^2/2D \qquad (1)$$

where l is the diffusional distance in question. In a system including a bed of target cells covered by a layer of liquid containing the vectors, the diffusional distance is the depth of the liquid layer containing the vectors which covers the target cells. D is the diffusion coefficient. The numerical value of the diffusion constant for a vector can be estimated from the Stokes-Einstein equation:

$$D = \frac{k_B T}{6\pi \mu R_o} \qquad (2)$$

where $k_B$ is the Boltzmann constant ($1.38 \cdot 10^{-16}$ erg/°K.); T=310° K., $\mu$ is the medium viscosity (about 1 cP for water and cell culture medium) and $R_o$ is hydrodynamic radius of the virus. For murine amphotropic virus $R_o$ is about 0.05 microns. Substituting these numerical values into the above equation one obtains D=$4.5 \cdot 10^{-8}$ cm²/sec. This value is about one one-hundredth of typical values for small organic molecules, such as glucose, and about one tenth of that observed for proteins. Thus, the average time for a murine amphotropic virus to diffuse 3 mm to the cell bed is $$t_{diff} = l^2/2D = 10^6 \text{ seconds} \qquad (3)$$

or about 11.5 days.

The half-life ($t_{0.5}$) of retroviruses is short. The half-life for the retrovirus produced by the CRIP cell line, used for the experiments reported below, has been measured as 5.5 hours. B. A. Shen et al., "Kinetics of Retroviral Production from the Amphotropic ψCRIP Murine Producer Cell Line," *Biotech & Bioeng*, (in press).

Based on the diffusion constant and the decay time, one can estimate the distance that an average viral vector can travel before one half-life has passed:

$$l_{0.5} \simeq \sqrt{2D \cdot t_{0.5}} \simeq 400 \text{ microns} \qquad (5)$$

This distance is short compared to the usual depths of liquid that are used in standard infection protocols. In fact, if one uses four half-lives in the above equation, one finds out that over 93% of the viruses have fallen apart after diffusing only 800 microns. Thus, in a typical infection procedure, in which the liquid layer is about 3000 microns (i.e., 3 mm) those virions beyond about 500 to 800 microns from the target cell have small probability of ever encountering the cell.

Thus, diffusion limits the average distance a vector can travel in solution in a given period of time. For vectors with short half-lives, such as retroviruses, diffusion limits the absolute number of contacts between vectors and target cells in a system comprising them.

This invention overcomes the diffusion-imposed limit on the rate and number of contacts between vectors and target cells by causing the vectors to move towards stationary target cells in an apparatus containing them, that is, by imparting a directed, biased or non-random motion to the vectors in the direction of the target cells. As a result of moving the vectors towards cells, they acquire a positive net velocity in the direction of the target cells in contrast to the zero net velocity of the vectors in solution due to Brownian motion.

The methods of this invention include causing the vectors to move in the direction of the cells by (1) causing flow-through of a liquid containing the vectors through or past a cell bed, (2) moving charged vectors towards the target cells by electrodiffusion and (3) centrifuging vectors and cells to cause settling of vectors onto the cells.

As used herein, the term "vector" means any particle capable of transferring a gene to a target cell in the infection process. Vectors known to the art include, for example, viruses, spheroplasts or liposomes containing genes, and free nucleic acids containing genes, such as plasmids or nucleic acid fragments.

Viruses useful in the methods of this invention include retroviruses (such as murine amphotropic virus), baculovirus, SV40-type viruses, polyoma viruses, adenoviruses, Epstein-Barr viruses, herpes simplex virus, vaccinia viruses and papilloma viruses. M. Krieger, *Gene Transfer and Expression: A Laboratory Manual*, W. H. Freeman and Company, New York, N.Y. (1990) and *Methods in Enzymology*, vol. 185, articles 38–44 (D. V. Goeddel, ed.) (1990), both incorporated herein by reference, further describe these vectors and their use. One can readily employ other vectors not named but known to the art.

The methods of this invention are particularly useful for increasing rates of infection by vectors having half-lives of less than 24 hours, such as the murine amphotropic virus and baculovirus. However, they are also useful for increasing rates of infection for vectors having longer half-lives. Adsorption of vectors by cells depends, in part, on concentration of the vector in solution. By imparting directed motion to the vectors in the direction of the cells, the methods of this invention effectively increase the concentration of the vectors in the vicinity of the cells, resulting in more adsorption and infection.

As used herein, the term "target cell" refers to cells supported on a surface and capable of being infected by a vector. Cells useful for gene therapy are particularly useful in this invention. They include, for example, bone marrow cells, lymphocytes, fibroblasts, keratinocytes, hepatocytes, endothelial cells, neurons, muscle cells, and epithelial cells. According to one embodiment, this invention uses hematopoietic stem cells, particularly of human origin. This invention further contemplates use of cells taken from a patient or subject with the intent of infecting those cells and re-introducing them into the patient or subject.

The target cells of this invention are substantially stationary with respect to the surface of the apparatus that supports them. Target cells can be attached cells, such as fibroblasts or stem cells. They also can be suspension cells which have settled onto the surface.

This invention is directed to methods of causing the vectors to move towards the stationary target cells by causing the liquid containing the vectors to flow past stationary target cells, for example, past or through a cell bed. Flow-through of liquid is also referred to as "convective flow" or "bulk flow."

In one embodiment of the flow-through method, the apparatus comprises a container having a porous surface which supports the target cells, and the container contains the liquid in contact with the porous surface. The vectors are moved towards the target cells by causing the liquid to flow through the porous surface. FIG. 1 depicts this embodiment.

It has been found that porous surfaces having pores large enough to allow passage of the vector are effective in this invention. Smaller pores tend to become clogged with the vector, especially in high retroviral titer supernatents. Porous surfaces having pores small enough so that the target cells cannot pass through are effective. In practice, this is a pore size range of about 0.1 microns to about 2 microns.

The effective viral motion is the average fluid velocity, given by the volumetric flow rate divided by the porous surface area. Flow rates above 0.01 cm/hr overcome the viral motion due to diffusion. The flow rate also should be slow enough to avoid shearing of the cells. Effective flow rates include between about 0.01 cm/hr to about 1.0 cm/hr, and flow rates above about 0.1 cm/hr are most efficient.

Cells should not be exposed to flow-through so long that they have significant decrease in viability. While this time will vary depending on cell lines, flow-through may proceed effectively for about 1 hr to about 10 hrs. It has been found that exposing CV-1 cells to flow-through for 2 to 3 hours does not decrease viability.

Cells usefully can be seeded at density of about 5% to about 90% of confluence on the porous surface. High density tends to block pores and decrease flow. However, this limitation is overcome by using larger pore sizes when cells are plated at higher density. After plating target cells on the porous surface, the liquid medium containing the vector is added. The liquid is then caused to flow past the cells.

In any of the methods of this invention, when cells are transfected with retroviruses at densities greater than about 50% confluency, it is preferable to transfer them after infection to lower density at which growth can occur and the retrovirus can integrate into the host gemone.

This method offers the advantage that the cell bed can be oxygenated from below since the lower surface of the membrane is exposed to the atmosphere. Such oxygenation may be advantageous when one uses higher cell densities on the membrane. It may also be useful to stimulate cell division, which is necessary for retroviral integration into the target cell's DNA.

A cell culture insert of about 6 ml makes a suitable container in this embodiment. A cell culture insert is a cup having a filtration membrane as the bottom surface, constituting the porous surface. "TRANSWELL®" (Costar, Cambridge, Mass.) or "FALCON" cell culture inserts (Becton Dickinson, Lincoln Park, N.J.) are useful in this invention as the container.

Figure 2:
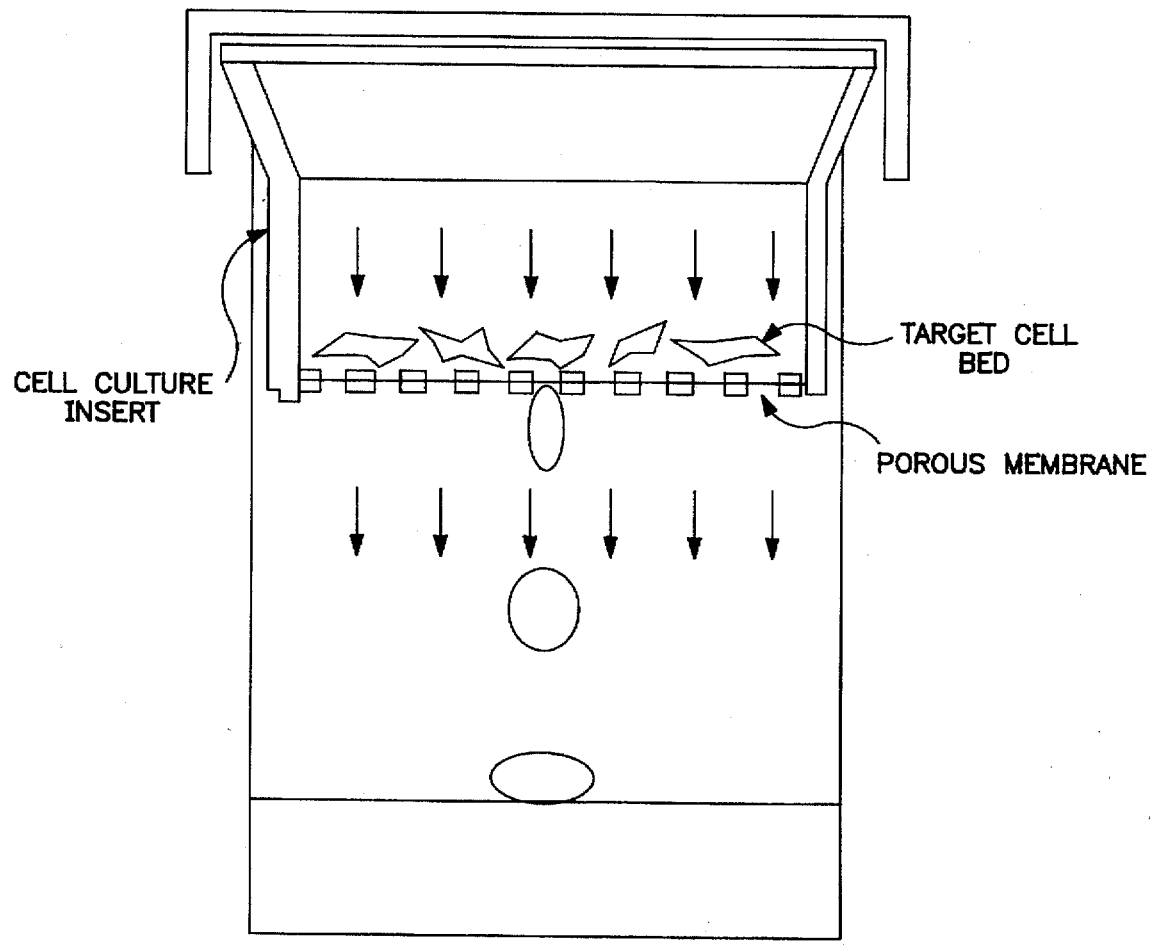
FIG. 2 depicts an embodiment of this invention in which liquid infection medium flows past the target cell bed and through the porous membrane by force of gravity. The container in this Figure is a cell culture insert.

When using a cell culture insert as the container, the system can be placed into the well of a culture dish to allow filtration and to collect the fluid. Convective flow of the liquid can proceed by allowing it to move under the force of gravity created by hydrostatic head. In this method, the liquid infection medium is added to the container and allowed to drip past the cells and through the porous surface. One factor effecting the rate of flow is the height of the liquid added to the container. FIG. 2 depicts this embodiment.

Figure 3:
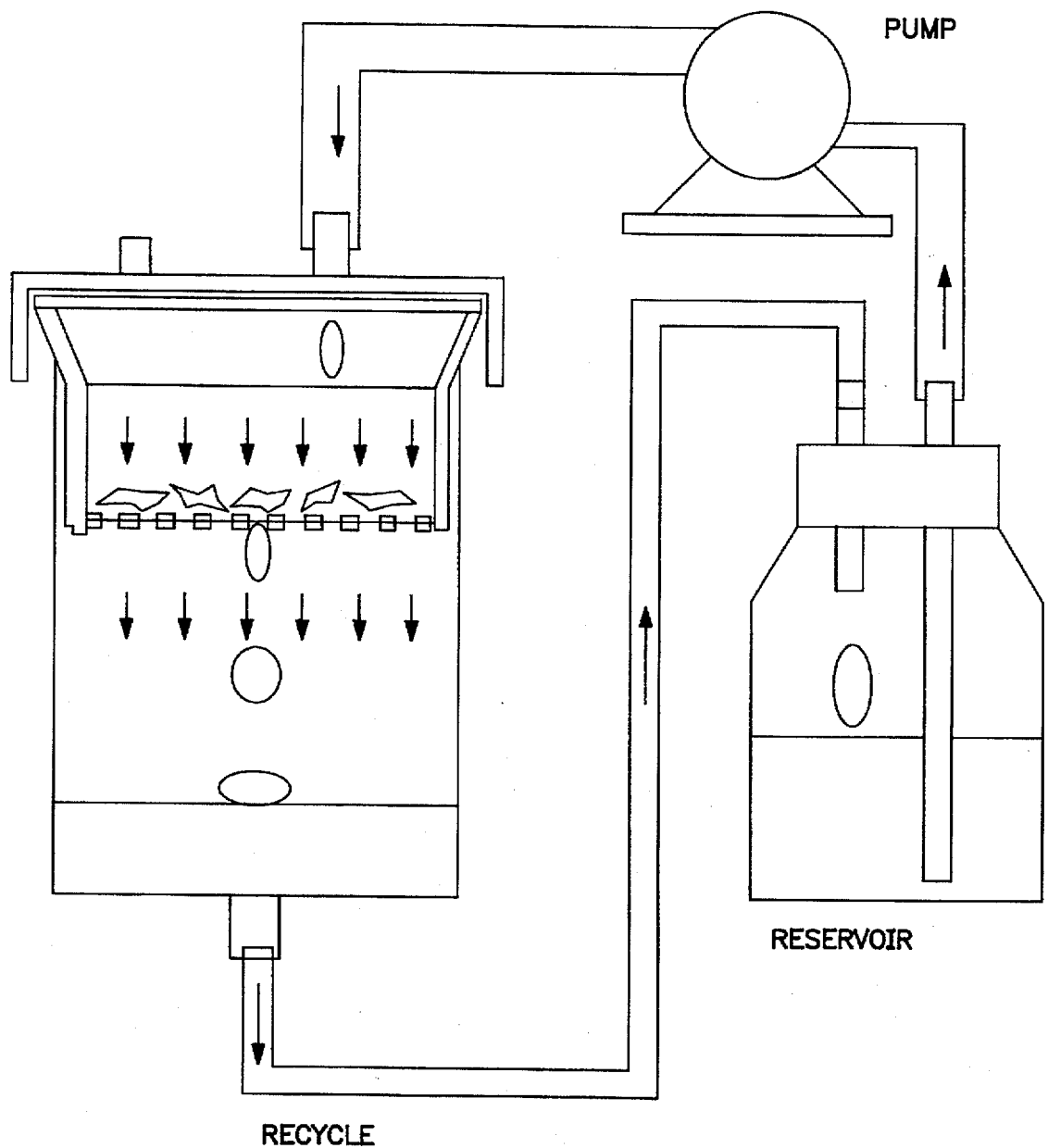
FIG. 3 depicts an embodiment of this invention in which liquid infection medium is recycled into the container. A pump draws medium that has already flowed past the cells into a reservoir and pumps the liquid back into the container.

One can increase the rate of infectivity by continually adding new medium containing the vector to the system, including recycling liquid that has already flowed through and that still contains vectors. FIG. 3 depicts this embodiment.

Figure 4:
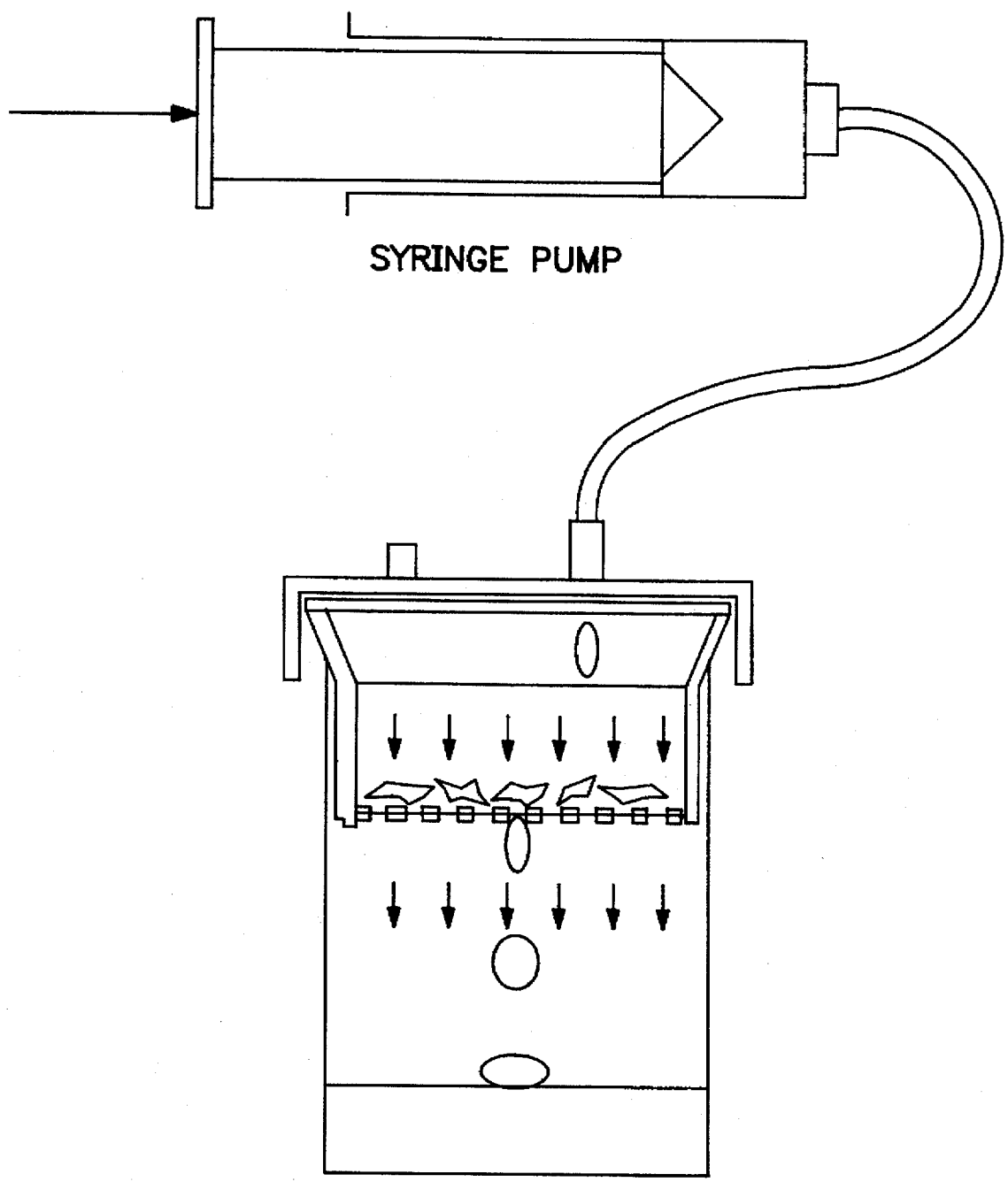
FIG. 4 depicts an embodiment of this invention in which a liquid containing the vector is moved past the target cells by flow-through using positive pressure. A syringe pump connected to the container above the liquid supplies the pressure.

Convective flow can also proceed by applying positive pressure. In one embodiment of this method, the apparatus further comprises a pump operably attached to a reservoir holding the liquid. The apparatus container is closed and the pump pumps the liquid from the reservoir into the container under pressure. The pressure range cannot be so great as to harm the cells. FIG. 4 depicts this embodiment.

Figure 5:
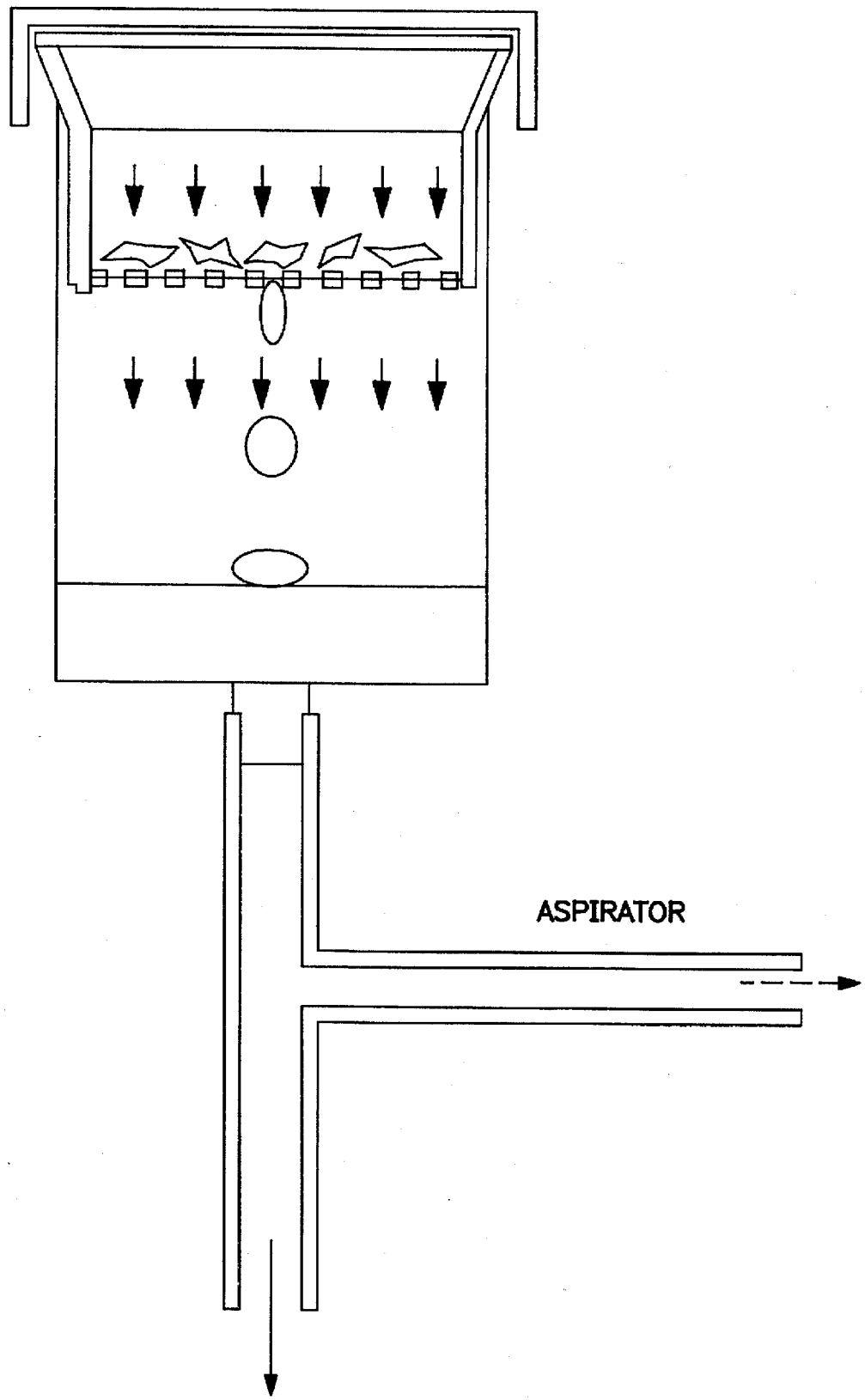
FIG. 5 depicts an embodiment of this invention in which a liquid containing the vector is moved past the target cells by flow-through using negative pressure. An aspirator connected to the container below the liquid supplies the suction.

Convective flow can also proceed by applying negative pressure (i.e., suction). In one embodiment of this method, the apparatus further comprises a pump operably attached to a space below the surface which supports the cells. The pump sucks liquid past the cells and through the porous surface. FIG. 5 depicts this embodiment.

Figure 6:
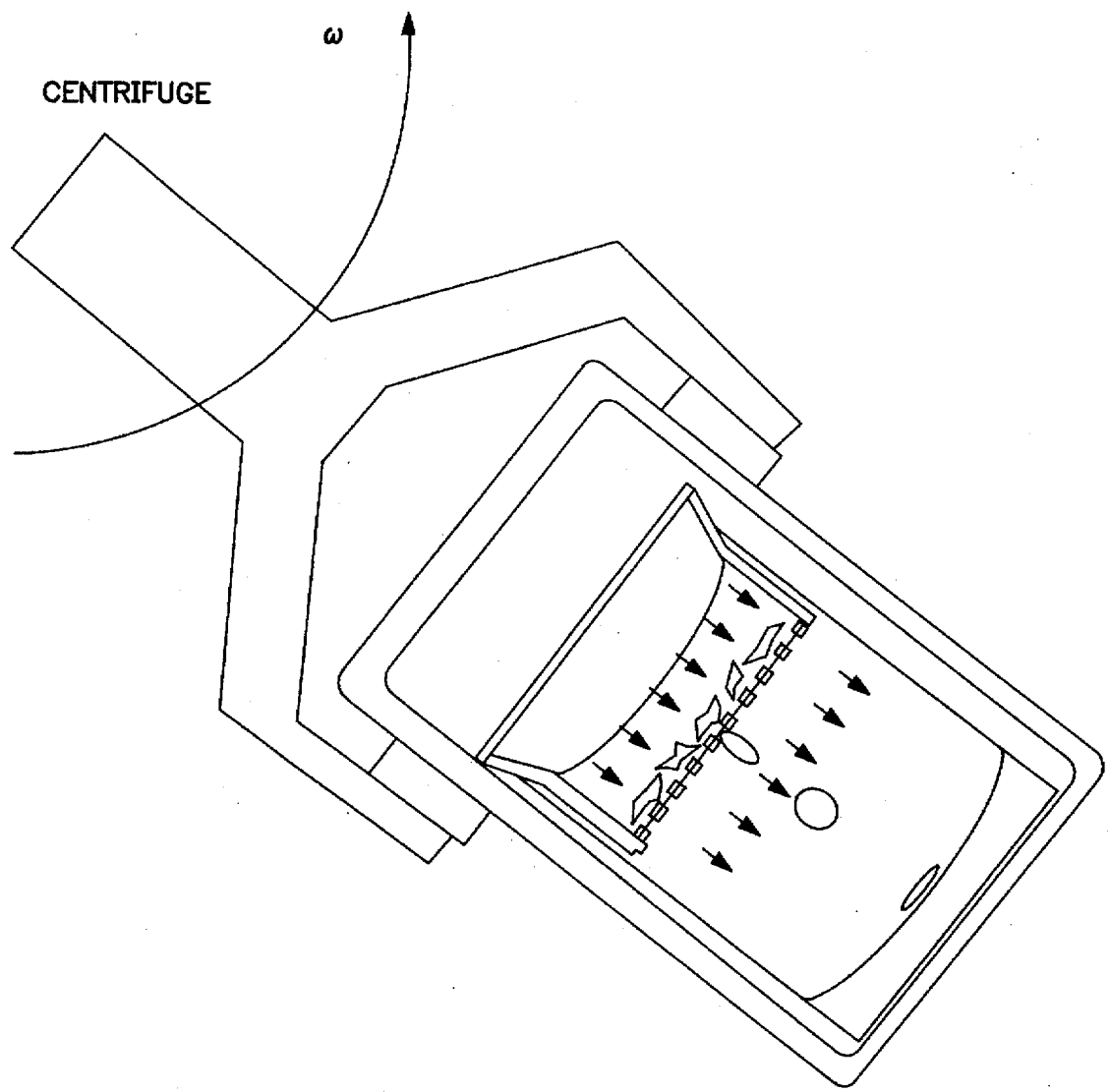
FIG. 6 depicts an embodiment of this invention in which the liquid infection medium is caused to flow past the target cell bed by enhanced gravity. The container is placed in the rotor of a centrifuge and spun around an axis in the direction of the arrow.

Convective flow can also proceed by applying enhanced gravitational force to the liquid. In this embodiment, the apparatus further includes a centrifuge for spinning the container. The process of centrifugation causes the liquid to pass through the filtration membrane faster than it does due to gravity alone. Centrifuges adapted for spinning culture dishes holding the container include the "BECKMAN MODEL G56®" (Palo Alto, Calif.) and the SORVALL RT-6000® by DuPont (Wilmington, Del.). The containers usefully are spun for less than about 5 minutes at less than about 100 g. FIG. 6 depicts this embodiment.

Figure 7:
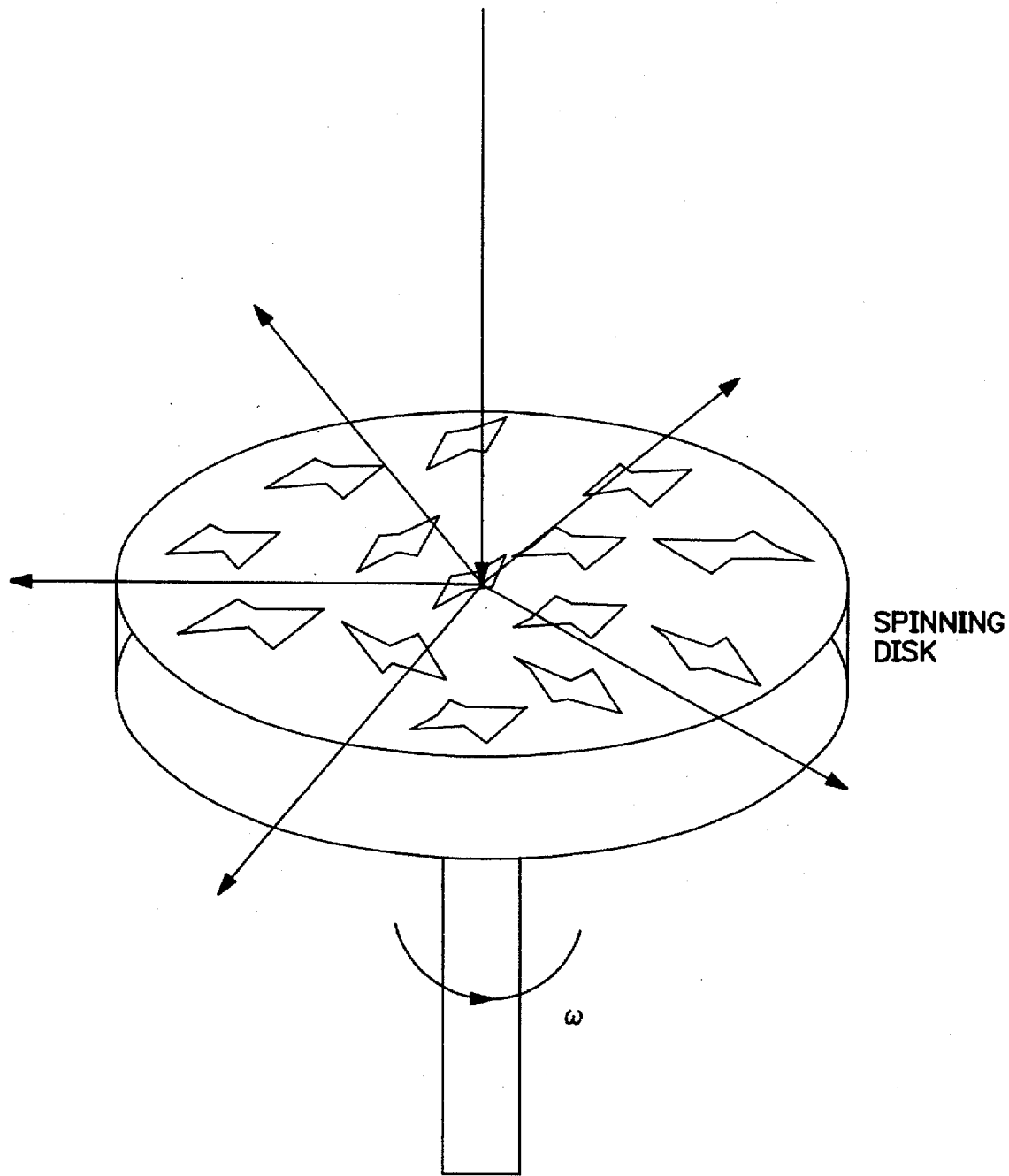
FIG. 7 depicts an embodiment of this invention involving a spinning disk. The disk on which the target cell bed is plated spins around an axis of rotation. Liquid infection medium is directed toward the surface of the disk as indicated by the heavy arrow. The liquid spreads out over the surface of the disk and comes into contact with the cell bed as indicated by the light arrows.

The spinning disk apparatus can be used to enhance retrovirus transport to the target cells. The apparatus includes target cells plated on the face of a spinable disk. Such disks are used in the pharmaceutical industry to measure diffusion of compounds into a liquid. See, e.g., Cussler, 1984, supra, pages 75–78. The step involves spinning the disk around an axis of rotation essentially perpendicular to the face of the disk, and directing a stream of liquid medium containing the vector toward the cells and substantially along the axis of rotation. When the medium hits the cells at the center of the disk, it spins out over the surface of the disk and past the target cells. FIG. 7 depicts this embodiment.

The rate of viral transport to the cell surface will increase with the square root of the angular velocity. Thus, the higher the rotation rate the more viruses that reach the target cells. The maximum rotation speed will be limited, however by the shear sensitivity of the target cells. The shear sensitivity of different types of cell varies greatly. Thus, the rotation rate and the flow velocity of the approaching fluid have to be such that the target cells are not damaged. The shear rate experienced by the target cells is expected to be below about 200 per second.

Figure 8:
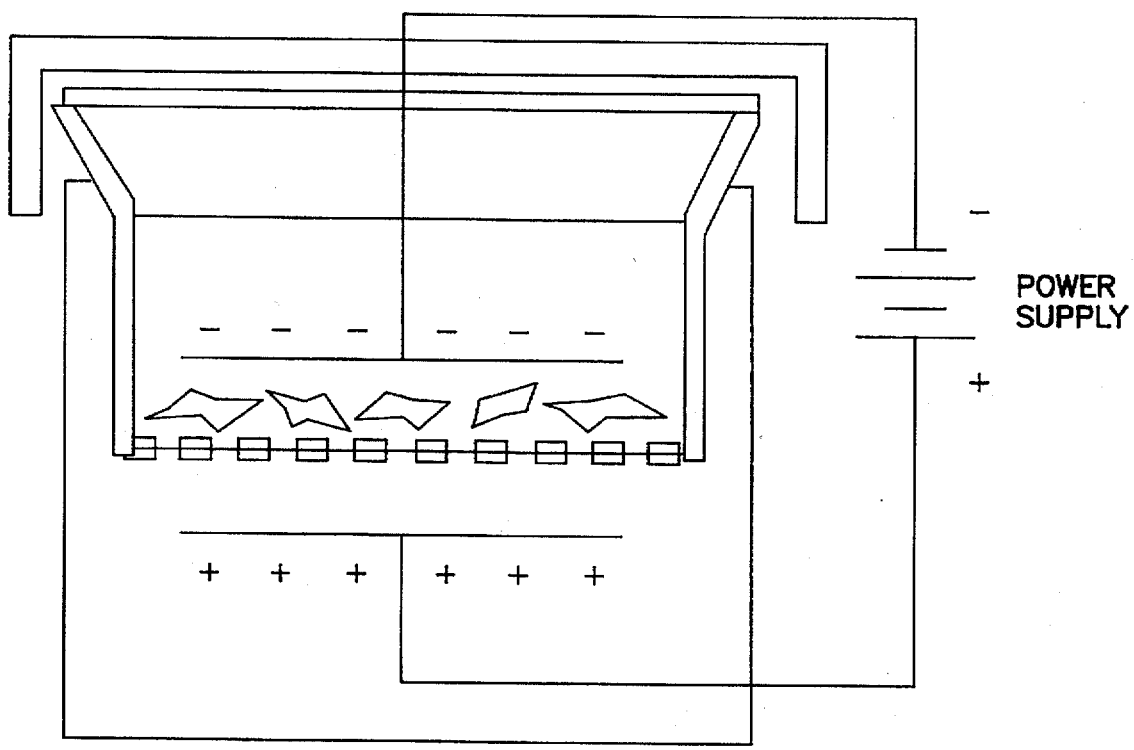
FIG. 8 depicts an embodiment of this invention in which the vectors are moved towards the target cells by electrodiffusion. An electrophoresis chamber includes a container with a permeable membrane on which the target cells are plated includes the liquid infection medium and a negative electrode. The chamber also includes a positive electrode in contact with electrophoresis buffer on the other side of the membrane. A power supply supplies the electrostatic force.

This invention is also directed to a method of causing the vectors to move towards the cells by applying electrostatic force. Viruses bear a net negative charge and can be moved by electrodiffusion. In this embodiment, the apparatus includes an electrophoresis unit having first and second chambers separated by an ion-permeable membrane. The first chamber contains an electrolytic fluid and a negative electrode in contact therewith. The second chamber contains an electrolytic fluid and a positive electrode in contact therewith. The apparatus also contains means for applying voltage across the positive and negative electrodes. The apparatus contains negatively charged vectors and target cells supported by the ion-permeable membrane in the first chamber. FIG. 8 depicts this embodiment.

Cells are seeded at low density on the ion-permeable membrane. However, this density can be greater than the density used in the flow-through methods, since it does not involve flow of liquid through a porous surface. Electrodiffusion is achieved by applying a voltage across the positive and negative electrodes of between about 1.5–10 volts for less than about 2 hours. While increased voltage will increase the velocity of the vectors towards the cells, the amount of increased voltage is limited by the damage that current causes to the vector and to the cell. Voltage can be applied intermittently or periodically to improve cell viability.

This invention is also directed to methods of causing the vectors to move towards the target cells by centrifugal force. Most retroviruses have a diameter of about 0.1 micron. Solutions containing them are essentially colloidal and the effective settling velocity of the virus is negligible compared with diffusion in a normal gravitational field. However, centrifugation of the medium at up to 1000 g will cause the virus to settle out at rates that exceed depletion by viral decay close to the cell bed. For example, 100 g will generate a sedimentation velocity of 0.015 cm/hr, approximately the minimum to overcome diffusion.

Figure 9:
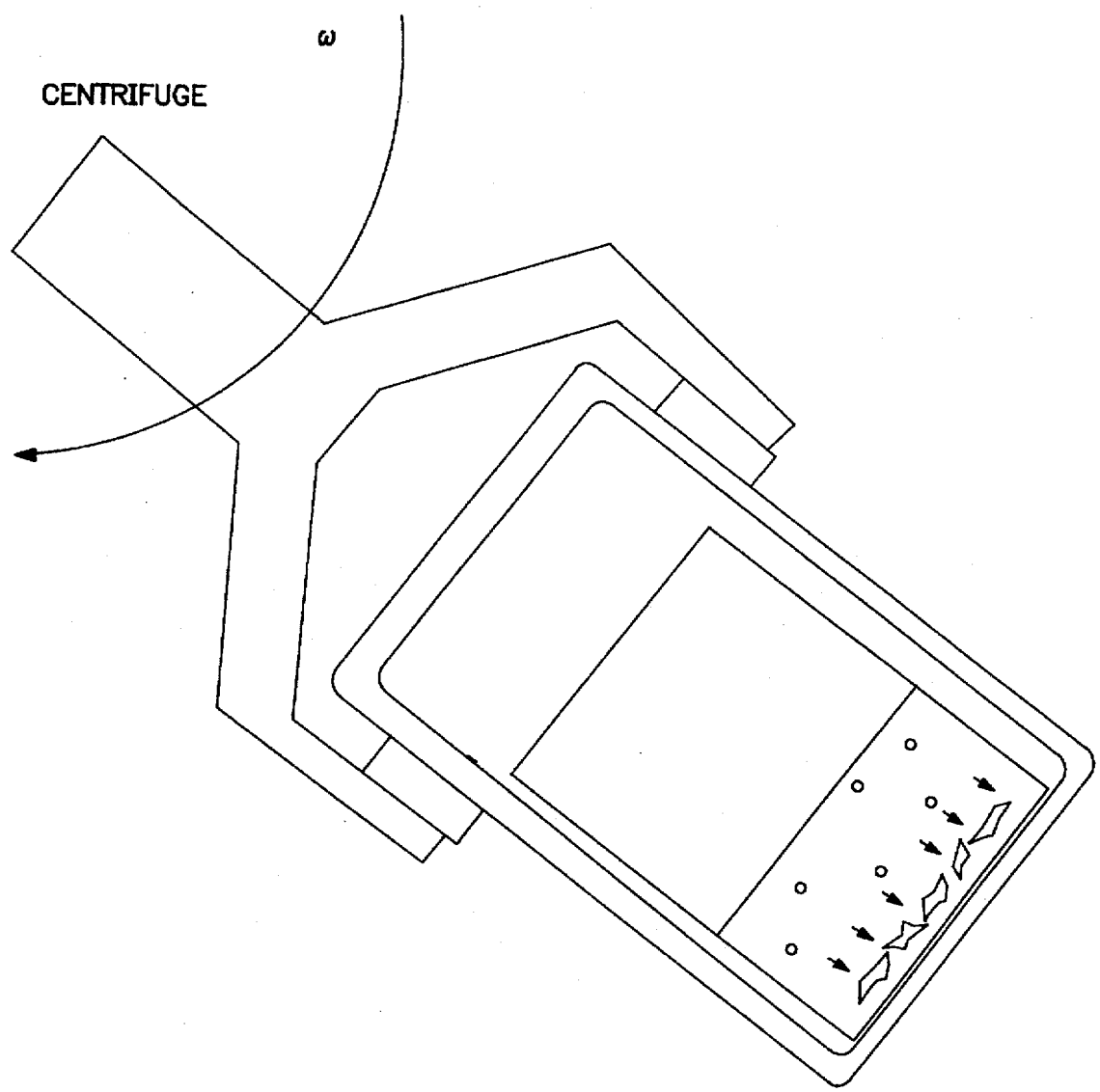
FIG. 9 depicts an embodiment of this invention in which the vectors are caused to move towards the target cells by means of centrifugal force in a centrifuge.

According to this embodiment, the apparatus includes a centrifuge. The cells in the centrifuge are supported on a surface at the bottom of the gravitational field so that the vectors settle out of the medium onto the cells. FIG. 9 depicts this embodiment.

Cells are seeded onto the surface of multiwell plates at 5% to 100% confluency (and preferably above 50%) with the infection medium. Then the plates are centrifuged in, for example, a "BECKMAN MODEL G56®" (Palo Alto, Calif.) or a "SORVALL RT-6000®" (Du Pont, Wilmington, Del.) centrifuge at between about 100 g and about 1000 g for less than about 2 hours. After the infection period, the cells can be re-plated at lower confluency (e.g. less than 50 %) and incubated under normal growth conditions so that they can grow to confluence.

EXAMPLE I

Diffusion of Virions in Solution

Data presented in this example on infection as a function of time and volume for the same concentration virus solution indicate that there is no gain in number of infected colonies with increasing amounts of virus applied to an adherent target cell bed. This finding shows that virus infection is limited by diffusion in the current method of infection (overlaying the target cells with a stagnant layer of infection solution).

Four liquid depths: 520 μm (500 μL), 832 microns (800 μL), and 1558 microns (1500 μL) were used to infect target cells seeded in six-well plates (surface area 9.62 cm$^2$) over 30 hours. The target cells were seeded in triplicate approximately 26 hours prior to each infection at 30,000 cells/well.

Eighteen 6-well plates were used. Duplicate cultures were also sacrificed for cell counts over 2–16 hours. Cell samples were obtained by washing cultures twice with 2 mL HBSS (Hanks Balanced Salt Solution) followed by incubation with 0.5 mL trypsin-EDTA. Cells were collected after they were rounded up and detached from the plates, and then they were counted on the hemocytometer.

The infection solution was obtained from 5 cultures of 60%–90% confluent ψCRIP/pMFG at cell passage #17. Cells were grown in Dulbecco's Modified Eagle's Medium (DMEM) ("GIBCO", cat. no. 430-2800EB) supplemented with 10% fetal bovine serum (FBS) ("GIBCO", cat. no. 240-6000AJ) or 10% calf serum supplemented (CSS) ("GIBCO", cat. no. 200-6160AJ) to 50% to 60% of confluence before the medium was totally replaced by fresh medium. Ten Petri dishes were "boosted" with fresh medium 24 hours previous, passed through conditioned 0.45 μ filters, and diluted approximately by half with fresh 10% CSS in DMEM. Polybrene was added to 4 μg/mL. Cells were overlaid with infection solution within 1.5 hours after supernatant was collected. Cell counts were performed in parallel wells to ensure that the cell growth was similar at all depths.

Infection was stopped by removing infection medium and adding 2 mL fresh medium after the incubation time. This process took less than seven minutes for each sample. Cultures were stained 4–5 doublings after infection, allowing plenty of time for expression of the integrated gene. Integration has been reported to take place 0.3 to 3 days post infection. D. R. Lowy, "Transformation and Oncogenesis: Retroviruses" in Virology, B. N. Fields et al., eds., Raven Press New York (1985).

The rounded average number of blue colonies in three trials as a function of the time the cells were exposed to infection medium are given in Table I below.

TABLE I

| Infection | Average Number of Colonies | | |
|---|---|---|---|
| Time (hrs) | Liquid depth 520 microns | Liquid depth 832 microns | Liquid depth 1558 microns |
| 0 | 0.7 | 0.3 | 0.3 |
| 2 | 43 | 52 | 35 |
| 4 | 56 | 48 | 49 |
| 6 | 68 | 69 | 81 |
| 8 | 72 | 63 | 98 |
| 11 | 110 | 99 | 96 |
| 14 | 129 | 96 | 93 |
| 18 | 139 | 103 | 117 |
| 24 | 102 | 97 | 104 |
| 28 | 98 | 94 | 137 |
| 33 | 129 | 129 | 129 |

These results show no increased infection with increasing liquid depth. Thus, the viruses that are added to the wells but are located at a distance exceeding about 520 microns do not reach the target cells in significant numbers and thus infection is not increased. Therefore only the viruses that are located close to the cell bed initially can reach the target cells and cause infection before they are inactivated. The process of retroviral infection is thus diffusion limited.

EXAMPLE II

Passing Virions Through a Porous Surface

Flowing infection solution past a cell bed dramatically increased the rate of infection compared to cultures with static fluid.

In a first experiment, 1.5 mL and 4 mL of a virus-containing supernatant were added to a 0.4 micron collagen membrane inserts ("TRANSWELL®","COSTAR") seeded with CV-1 target cells one day previous at 30,000 cells per "TRANSWELL®" insert. These "TRANSWELL®" inserts were suspended separately above an aseptic vial that collected the fluid that flowed through the membrane. Each insert was filled with fluid and flow was induced by gravity. 1.5 mL was also added to a seeded insert with an additional 3.2 mL in the well below so that the liquid levels remained equal, and thus no flow would be induced (static culture reference point).

After 8.5 hours of exposure, 0.35 mL remained in the insert from 1.5 mL originally added (about 1.15 mL flowed through), and 1.4 mL remained from the 4 mL originally added (about 2.6 mL flowed through). The static culture control contained about 1.5 mL. Hank's balanced salt solution (HBSS) was used to wash the inserts before fresh growth medium was added. The extent of infection was determined by counting the number of blue cells as described in Example I.

The results are shown in Table II. This presents the relative infectivities as a function of volume of liquid flowed through. Because different heights of liquid were used, these results represent flow rates of about 0.1 cm/hr to 0.2 cm/hr.

TABLE II

| flow (ml) | fraction blue cells | relative infectivities (to static cultures) |
| --- | --- | --- |
| 0.000 | 0.014 | 1.000 |
| 1.500 | 0.100 | 7.143 |
| 3.000 | 0.260 | 18.571 |
| 3.900 | 0.400 | 28.571 |
| 4.500 | 0.380 | 27.143 |

Thus, with modest flow of infection medium through the cell bed almost 30-fold increase in the number of infected cells was observed.

In a second experiment, a range of infection solution volumes (1–6 mL) was added to seeded inserts suspended above aseptic vials, as described above. Static cultures containing 2 mL infection solution in the insert and approximately 3 mL in the wells were used as controls. Virus-containing supernatants were used in the static cultures and on the suspended inserts. Approximately 1–6 mL infection solution flowed through the inserts and no effective volume flowed through the static control during the 9 hour infection period. Cultures were treated as in the prior experiment after this point.

The results are shown in Table III. Again, because different heights of liquid were used, these results represent flow rates of between about 0.1 cm/hr and about 0.2 cm/hr.

TABLE III

| flow (ml) | fraction blue cells | relative infection rate (to static cultures) |
| --- | --- | --- |
| 0.000 | 0.032 | 1.000 |
| 1.000 | 0.083 | 2.594 |
| 1.000 | 0.102 | 3.188 |
| 2.000 | 0.204 | 6.375 |
| 2.000 | 0.222 | 6.938 |
| 2.300 | 0.241 | 7.531 |
| 2.400 | 0.337 | 10.531 |
| 4.000 | 0.436 | 13.625 |
| 4.000 | 0.401 | 12.531 |
| 5.000 | 0.552 | 17.250 |
| 5.000 | 0.394 | 12.312 |
| 6.000 | 0.523 | 16.344 |
| 6.000 | 0.515 | 16.094 |

In this experiment about 16 to 17 fold increase in infection rate was observed. The difference between these results and the previous experiment are probably due to differences in viral titer.

Although the invention has been described with reference to the presently-preferred embodiment, it should be understood that various modifications can be made without departing from the spirit of the invention. Accordingly, the invention is limited only by the following claims.

We claim:

1. A method of infecting or transfecting target cells by vectors, comprising the steps of:

(a) putting the target cells on a porous surface; and (b) directing the vectors to contact the target cells by moving a liquid containing the vectors through the porous surface, wherein the porous surface has pores that are large enough to allow the vectors to pass through but small enough to prevent the target cells from passing through, the target cells are substantially stationary with respect to the porous surface, and the number of contacts between the target cells and the vectors is greater than that due to Brownian motion of the vectors in the liquid.

2. The method of claim 1, wherein the pores are between about 0.1 microns and about 2 microns in diameter.

3. The method of claim 1, wherein the porous surface is a cell culture insert.

4. The method of claim 1, wherein the vectors are selected from the group consisting of viruses, sphereoplasts containing genes, liposomes containing genes and free nucleic acids containing genes.

* * * * *

UNITED STATES PATENT AND TRADEMARK OFFICE
CERTIFICATE OF CORRECTION

PATENT NO.   : 5,672,494
DATED        : Sep. 30, 1997
INVENTOR(S)  : Palsson et al.

It is certified that error appears in the above-identified patent and that said Letters Patent is hereby corrected as shown below:

In column 1, line 51, please delete "direct to" and replace therefor with --direct--.

In column 5, line 57, please delete "gemone" and replace therefor with --genome--.

In column 10, line 39, please delete "through," and replace therefor with --through;--.

In column 10, line 40, please delete "surface," and replace therefor with --surface;--.

Signed and Sealed this

Tenth Day of April, 2001

*Attest:*

NICHOLAS P. GODICI

*Attesting Officer*    Acting Director of the United States Patent and Trademark Office